United States Patent
Sato (10) Patent No.: US 11,304,627 B2
(45) Date of Patent: Apr. 19, 2022

(54) BALANCE TRAINING APPARATUS AND CONTROL PROGRAM OF BALANCE TRAINING APPARATUS

(71) Applicant: Toyota Jidosha Kabushiki Kaisha, Toyota (JP)

(72) Inventor: Yoh Sato, Miyoshi (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 216 days.

(21) Appl. No.: 16/814,133

(22) Filed: Mar. 10, 2020

(65) Prior Publication Data
US 2020/0289035 A1   Sep. 17, 2020

(30) Foreign Application Priority Data
Mar. 15, 2019 (JP) .............................. JP2019-047885

(51) Int. Cl.
*A61B 5/11* (2006.01)
*A63B 23/00* (2006.01)
*A63B 26/00* (2006.01)

(52) U.S. Cl.
CPC .......... *A61B 5/1116* (2013.01); *A63B 26/003* (2013.01); *A63B 2220/13* (2013.01)

(58) Field of Classification Search
CPC . A61B 5/1116; A61B 2505/09; A61B 5/4023; A61B 5/1036; A63B 26/003; A63B 2220/13; A63B 22/20; A63B 71/0054; A63B 71/0622; A63B 2220/52; A63B 2220/80; A63B 2220/833; A63B 2225/02; A63B 2225/50; A63B 2230/625; A61H 2201/1215; A61H 2201/5007; A61H 1/0262; A61H 2201/5046; A61H 2201/5061; A61H 2203/0406; A61H 1/00
See application file for complete search history.

(56) References Cited

U.S. PATENT DOCUMENTS

| 18,249 | A | * | 9/1857 | Robertson | ................ | B41K 3/08 |
| | | | | | | 101/110 |
| 143,198 | A | * | 9/1873 | Taylor | ...................... | A41D 1/14 |
| | | | | | | 2/211 |
| 229,167 | A | * | 6/1880 | Morse | .................... | B60G 11/02 |
| | | | | | | 267/39 |

(Continued)

FOREIGN PATENT DOCUMENTS

| JP | 2015-100477 A | 6/2015 |
| JP | 2018-121911 A | 8/2018 |

*Primary Examiner* — Garrett K Atkinson
(74) *Attorney, Agent, or Firm* — Dinsmore & Shohl LLP (57) ABSTRACT

The balance training apparatus includes: a moving cart capable of moving on a moving surface by driving a driving unit; a detection unit configured to detect a load received from a foot of a trainee who is standing on the moving cart; a calculation unit configured to calculate the center of gravity of loads of both feet of the trainee on a riding surface from, the load detected by the detection unit; a setting unit configured to set the center of gravity of the loads at which it is estimated that the trainee has maintained an upright state on the riding surface as a reference center of gravity; and an instruction controller configured to output an instruction of the orientation of the body to the trainee and an instruction to move the center of gravity to the trainee.

6 Claims, 7 Drawing Sheets

(56) References Cited

U.S. PATENT DOCUMENTS

| | | | | |
|---|---|---|---|---|
| 3,408,067 A * | 10/1968 | Armstrong | A63B 22/02 | 482/30 |
| 4,204,673 A * | 5/1980 | Speer, Sr. | A63B 22/0012 | 198/817 |
| 4,423,864 A * | 1/1984 | Wiik | A63B 22/0012 | 434/253 |
| 4,733,858 A * | 3/1988 | Lan | A63B 23/1209 | 482/113 |
| 5,314,390 A * | 5/1994 | Westing | A63B 21/00178 | 482/111 |
| 5,830,162 A * | 11/1998 | Giovannetti | A61H 1/0229 | 601/23 |
| 6,880,487 B2 * | 4/2005 | Reinkensmeyer | A01K 15/027 | 119/421 |
| 7,125,388 B1 * | 10/2006 | Reinkensmeyer | A63B 69/0064 | 601/5 |
| 7,381,163 B2 * | 6/2008 | Gordon | A63B 22/02 | 482/69 |
| 7,621,850 B2 * | 11/2009 | Piaget | A63B 22/0056 | 482/54 |
| 7,980,856 B2 * | 7/2011 | Grabiner | A63B 22/0292 | 434/258 |
| 7,998,040 B2 * | 8/2011 | Kram | A63B 21/4013 | 482/124 |
| 8,002,674 B2 * | 8/2011 | Piaget | A63B 22/0056 | 482/52 |
| 8,550,962 B2 * | 10/2013 | Piaget | A63B 23/0429 | 482/52 |
| 8,738,278 B2 * | 5/2014 | Chen | B62K 11/007 | 701/124 |
| 9,403,573 B1 * | 8/2016 | Mazzei | B62D 61/08 | |
| 9,510,991 B2 * | 12/2016 | Stockmaster | A61H 3/008 | |
| 9,713,439 B1 * | 7/2017 | Wu | A61B 5/11 | |
| 9,801,775 B2 * | 10/2017 | Vallery | A61G 7/1042 | |
| 9,908,579 B2 * | 3/2018 | Zuo | B62M 7/12 | |
| 10,556,636 B2 * | 2/2020 | Chen | B62K 3/005 | |
| 2004/0143198 A1 * | 7/2004 | West | A61F 5/0102 | 601/5 |
| 2006/0229167 A1 * | 10/2006 | Kram | A63B 21/00181 | 482/54 |
| 2012/0018249 A1 * | 1/2012 | Mehr | A63B 69/0064 | 182/5 |
| 2012/0166048 A1 * | 6/2012 | Inoue | G05D 1/0238 | 701/49 |
| 2014/0206503 A1 * | 7/2014 | Stockmaster | A61H 3/008 | 482/4 |
| 2015/0320632 A1 * | 11/2015 | Vallery | A61G 7/1061 | 482/69 |
| 2016/0185412 A1 * | 6/2016 | Zuo | B62M 7/12 | 180/218 |
| 2016/0256346 A1 * | 9/2016 | Stockmaster | A61B 5/1117 | |
| 2017/0027803 A1 * | 2/2017 | Agrawal | A61B 5/224 | |
| 2017/0129523 A1 * | 5/2017 | Hane | A61H 3/04 | |
| 2017/0135893 A1 * | 5/2017 | Stockmaster | A61H 3/008 | |
| 2017/0225736 A1 * | 8/2017 | Chen | B62J 45/41 | |
| 2018/0055715 A1 * | 3/2018 | Vallery | A63B 21/4009 | |
| 2018/0165982 A1 | 6/2018 | Takahashi et al. | | |
| 2018/0334214 A1 * | 11/2018 | Cuban | B62K 11/007 | |
| 2019/0046373 A1 * | 2/2019 | Coulter | A61G 5/063 | |
| 2019/0092387 A1 * | 3/2019 | Ying | B62K 11/007 | |
| 2020/0289895 A1 * | 9/2020 | Sato | A63B 24/0062 | |

* cited by examiner

FRONT/BACK TRAINING MODE

RIGHT/LEFT TRAINING MODE

FRONT/BACK TRAINING MODE

RIGHT/LEFT TRAINING MODE

BALANCE TRAINING APPARATUS AND CONTROL PROGRAM OF BALANCE TRAINING APPARATUS

CROSS REFERENCE TO RELATED APPLICATIONS

This application is based upon and claims the benefit of priority from Japanese patent application No. 2019-047885, filed on Mar. 15, 2019, the disclosure of which is incorporated herein in its entirety by reference.

BACKGROUND

The present disclosure relates to a balance training apparatus and a control program of the balance training apparatus.

Training apparatuses for enabling patients who have disabilities in their legs to perform rehabilitation training have become more and more widespread. For example, a training apparatus, in which a trainee who performs training stands on a footplate, the centroid position of the trainee is observed, and the footplate is moved by driving means in order to encourage the trainee to step forward and to prevent the trainee from falling has been known (see, for example, Japanese Unexamined Patent Application Publication No. 2015-100477).

SUMMARY

In a configuration in which the footplate is moved by a small amount with respect to the training apparatus, the trainee basically maintains an upright state with respect to the floor surface. In this configuration, since there is hardly any environmental change, it is difficult for the trainee to maintain his/her motivation for the training. On the other hand, it has been revealed that a large movement of the moving cart in accordance with a movement of the center of gravity of the trainee for the purpose of changing the environment maintains or improves the trainee's motivation.

Further, in the balance training, besides training for recovery of balance functions of the trainee in the front-back direction, training for recovery of the balance functions of the trainee in the right-left direction may also be performed. When the direction of the balance training is changed, by changing the orientation of the body of the trainee while fixing the moving direction of the moving cart, both the balance training in the front-back direction and the balance training in the right-left direction can be performed. There is a problem, however, that appropriate balance training cannot be performed unless the balance training apparatus is able to check whether the orientation of the body of the trainee is directed to a direction in accordance with a training mode.

The present disclosure has been made in order to solve the aforementioned problem, and provides a balance training apparatus and the like for accurately determining the orientation of the body of the trainee who has disabilities in his/her balance function when he/she performs rehabilitation training.

A balance training apparatus according to a first aspect, of the present disclosure includes: a moving cart capable of moving on a moving surface by driving a driving unit; a detection unit configured to detect a load received from a foot of a trainee who is standing on the moving cart; a calculation unit configured to calculate the center of gravity of loads of both feet of the trainee on a riding surface from the load detected by the detection unit; a setting unit configured to set the center of gravity of the loads at which it is estimated that the trainee has maintained an upright state on the riding surface as a reference center of gravity; and an instruction controller configured to output an instruction of the orientation of the body to the trainee and an instruction to move the center of gravity to the trainee, in which the calculation unit determines the orientation of the body of the trainee based, on a change direction of the center of gravity of the loads from the reference center of gravity when the trainee has moved his/her center of gravity in accordance with the instruction from the instruction controller, and outputs an operation instruction to the driving unit when it is determined that the result of the determination is appropriate.

As described above, by determining the orientation of the body of the trainee before the training is started and giving the operation instruction to the driving unit when it is determined that the result of the determination is appropriate, it is possible to prevent inappropriate training from being provided for the trainee.

In the aforementioned balance training apparatus, the setting unit may set the reference center of gravity based on the center of gravity of the loads calculated by the calculation unit in a calibration operation that the trainee performs prior to trial of the training. Further, the instruction controller may output a center of gravity moving instruction to the trainee who is in an upright state to cause the trainee to move one foot, and the calculation unit may output the operation instruction to the driving unit when a displacement direction of the center of gravity of the loads of the trainee from the reference center of gravity after the instruction for moving the center of gravity is a direction along a preset displacement direction.

Further, the calculation unit may switch a training mode in which a frontal direction of the body of the trainee matches a moving direction of the moving cart and a right/left training mode in which the frontal direction of the body of the trainee is substantially orthogonal to the moving direction of the moving cart based on an external instruction.

Further, the calculation unit may instruct the instruction controller to display the position of the center of gravity of the loads of the trainee, and after it is determined that the center of gravity of the loads of the trainee remains in a preset measurement start position for a predetermined period of time, the calculation unit may instruct the instruction controller to cause the trainee to move the center of gravity.

Further, a control program of a balance training apparatus according to a second aspect of the present disclosure is a control program of a balance training apparatus in which a trainee who is standing on a moving cart that moves on a moving surface performs balance training, the control program causing a computer to execute the following steps: a center of gravity calculation step for calculating the center of gravity of loads of both feet of the trainee on a riding surface from the load detected by a detection unit mounted on the moving cart; a reference center of gravity setting step for setting, the center of gravity of the loads at which it is estimated that the trainee has maintained an upright state on the riding surface as a reference center of gravity; an instruction control step for outputting an instruction of the orientation of the body to the trainee and an instruction to move the center of gravity to the trainee; and a control determination step for determining the orientation of the body of the trainee based on a change direction of the center of gravity of the loads from the reference center of gravity when the trainee has moved his/her center of gravity in the instruction output in the instruction controller step and performing control to move the moving cart when it is determined that the result of the determination is appropriate. According to the balance training apparatus controlled by the aforementioned control program, as described above, by determining the orientation of the body of the trainee before the training is started and giving the operation instruction to the driving unit when it is determined that the result of the determination is appropriate, it is possible to prevent inappropriate training from being provided for the trainee.

According to the present disclosure, it is possible to provide the balance training apparatus and the like capable of accurately determining the orientation of the body of the trainee who has disabilities in his/her balance function when she/he performs rehabilitation training.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION

Hereinafter, the present disclosure will be explained with reference to embodiments of the present disclosure. However, the disclosure set forth in the claims is not limited to the following embodiments. Further, not all the structures explained in the embodiments may be necessary as means for solving the problem.

First Embodiment

Figure 1:
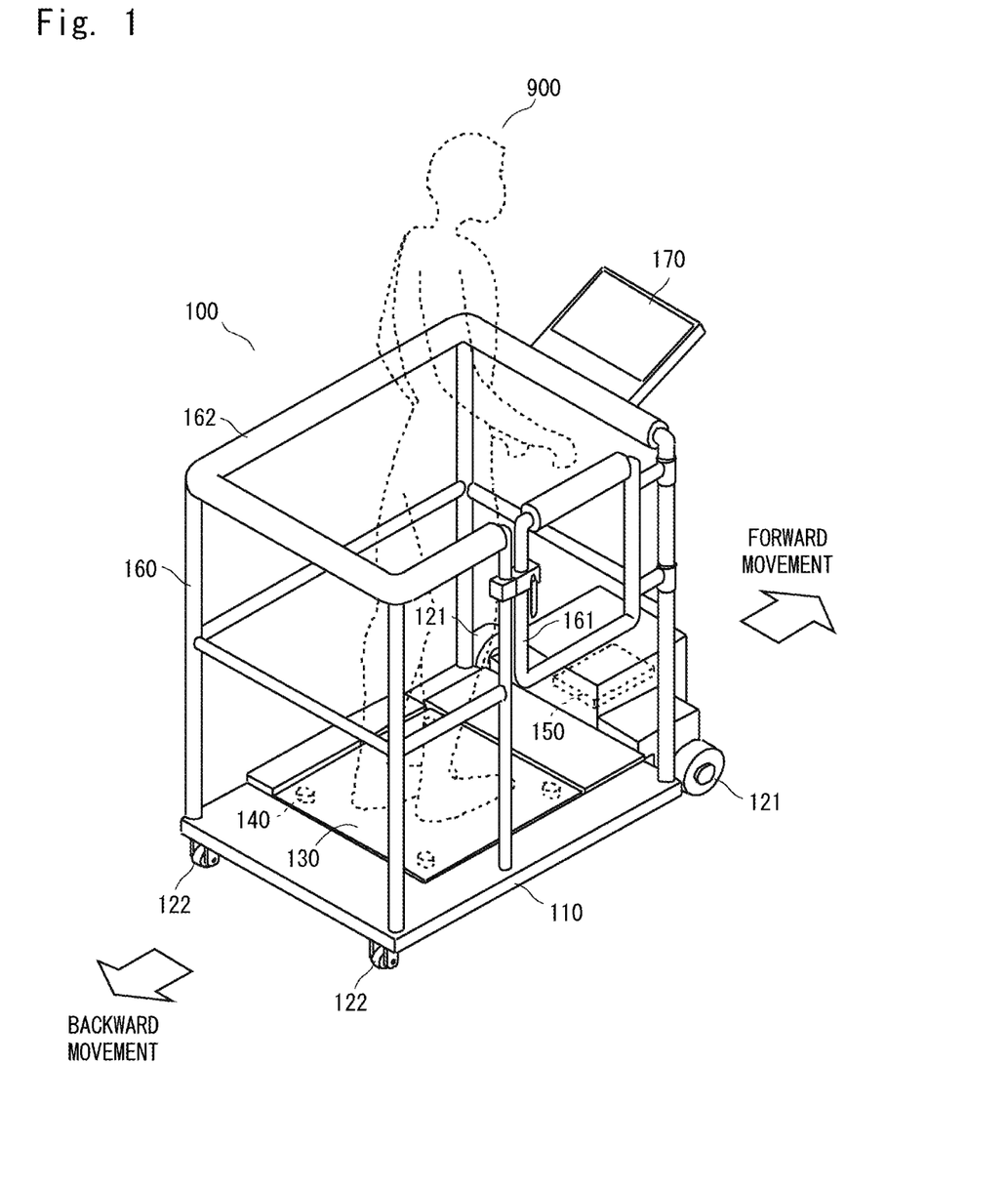
FIG. 1 is a schematic perspective view of a training apparatus according to a first embodiment.

FIG. 1 is a schematic perspective view of a training apparatus 100, which is one example of a balance training apparatus according to a first embodiment. The training apparatus 100 is an apparatus for enabling a disabled person having a disability such as hemiplegia to learn a centroid movement that is necessary for walking or enabling a patient who has a disability in his/her ankle joint to recover an ankle joint function. When, for example, a trainee 900 who desires to recover the ankle joint function continues to ride the training apparatus 100 while balancing himself/herself, the training apparatus 100 is able to give the ankle joint of the trainee 900 a load that can be expected to achieve rehabilitation effects.

The training apparatus 100 includes a moving cart 110 that can move on a moving surface, which is a floor surface or the like of a rehabilitation facility, in the front-back direction, and a frame 160 that is installed in the moving cart 110 and prevents the trainee 900 who rides the moving cart 110 from falling off. The moving cart 110 mainly includes driving wheels 121, casters 122, a riding, plate 130, load sensors 140, and a control box 150.

The driving wheels 121 are provided as two front wheels with respect to the traveling direction. The driving wheels 121, which are rotationally driven by a motor (not shown) provided as a driving unit, move the moving cart 110 forward or backward. The casters 122, which are trailing wheels, are provided as two rear wheels with respect to the traveling direction. The riding plate 130 is a riding part where the trainee 900 rides and puts his/her feet. The riding plate 130 is a flat plate made of, for example, polycarbonate resin having a relatively high rigidity that can withstand riding of the trainee 900. The riding plate 130 is supported on the upper surface of the moving cart 110 via the load sensors 140 arranged at four corners of the riding plate 130.

The load sensors 140, which are, for example, load cells, function as detection units configured to detect loads received from the feet of the trainee 900 who is standing on the moving cart 110. The control box 150 accommodates an operation processing unit and a memory that will be described later.

Figure 2:
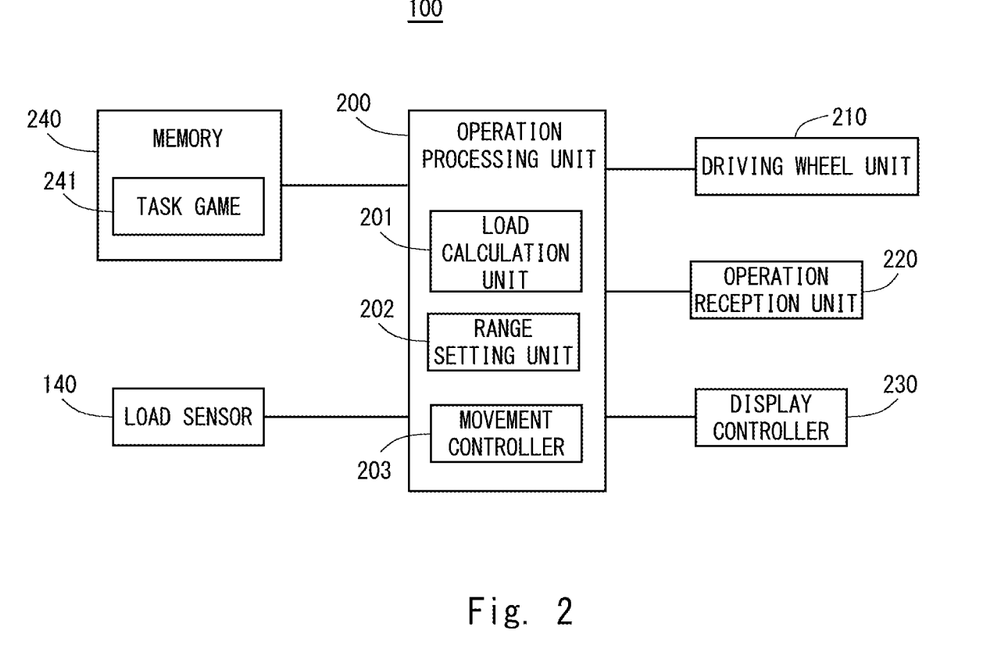
FIG. 2 is a diagram showing a system configuration of the training apparatus according to the first embodiment.

The frame 160 includes an opening door 161 and a handrail 162. The opening door 161 is opened when the trainee 900 rides the riding plate 130 and forms a passage where the trainee 900 passes. When the trial of the training is performed, the opening door 161 is closed and locked. The handrail 162 is provided so as to surround the trainee 900 so that the trainee 900 is able to hold the handrail 162 when he/she is about to lose his/her balance or when he/she feels unsafe. The frame 160 supports a display panel 170. The display panel 170, which is, for example, a display unit such as a liquid crystal panel, is provided in a position where the trainee 900 can easily see it during the trial of the training, FIG. 2 is a diagram showing a system configuration of the training apparatus 100, An operation processing unit 200, which is, for example, an MPU, executes a control program loaded from a memory 240, thereby executing control of the entire apparatus. A driving unit (e.g., a driving wheel unit 210) includes a driving circuit and a motor for driving the driving wheels 121, Further, the driving wheel unit 210 includes a rotary encoder configured to detect the rotation amount of the driving wheels 121.

An operation reception unit 220 accepts an input operation from the trainee 900 or an operator and transmits an operation signal to the operation processing unit 200. The trainee. 900 or the operator operates an operation button provided in the apparatus, a touch panel overlapped with the display panel 170, an attached remote control or the like that form the operation reception unit 220, thereby turning on/off the power supply, giving an instruction for starting the trial of the training, inputting numerical values regarding setting, or selecting a menu item.

A display controller 230 generates, for example, an instruction regarding the posture to be sent to the trainee 900, a graphic image of a task game or the like in accordance with a display signal, from, the operation processing unit 200, and displays the generated message or image on the display panel 170. The memory 240, which is a non-volatile storage medium, may be, for example, a solid state drive. The memory 240 stores a control program etc. for controlling the training apparatus 100. The memory 240 further stores various parameter values, functions, lookup tables and the like to be used for control. The memory 240 stores, in particular, a task game 241, which is a program for giving a task in a form of a game so as to allow the trainee 900 to enjoy performing the trial of the training. The load sensor 140 detects a load applied from the foot of the trainee 900 via the riding plate 130 and transmits the detection signal to the operation processing unit 200.

The operation processing unit 200, which is a calculation unit, also serves as a function execution unit configured to execute various operations and control of individual elements in accordance with a request from the control program. A load calculation unit 201 acquires detection signals of the four load sensors 140 and calculates the center of gravity of the loads of the respective feet of the trainee 900 on the riding surface. More specifically, since the respective positions of the four load sensors 140 are known, the centroid position is calculated front the distribution of the loads in the vertical direction detected by the respective load sensors 140, and this position is set as the center of gravity.

A range setting unit 202 sets the center of gravity of the loads at which it is estimated that the trainee 900 has maintained the upright state on the riding surface as a reference center of gravity. The determination regarding whether the trainee 900 has maintained the upright state on the riding surface is made by determining whether the center of gravity of the loads has been located within a range of stability, which is a preset range, for a predetermined period of time. A movement controller 203 generates a driving signal to be transmitted to the driving wheel unit 210 and controls the movement of the moving cart 110 via the driving wheel unit 210, in the first embodiment, in particular, it is switched whether to operate the driving wheel unit 210 based on the results of the determination regarding whether the orientation of the body of the trainee 900 is the one instructed to the trainee 900 by the display controller 230.

Now, a method of determining the reference center of gravity by the range setting unit 202 will be explained. The training apparatus 100 according to the first embodiment instructs the trainee 900 to maintain the upright state on the riding surface. At this time, the range in which the center of gravity of the loads of the trainee 900 detected by the load sensors 140 is displaced is within a predetermined magnitude. The range setting unit 202 sets, for example, the center of the range in which the center of gravity of the loads of the trainee 900 is displaced as the reference center of gravity.

Figure 3:
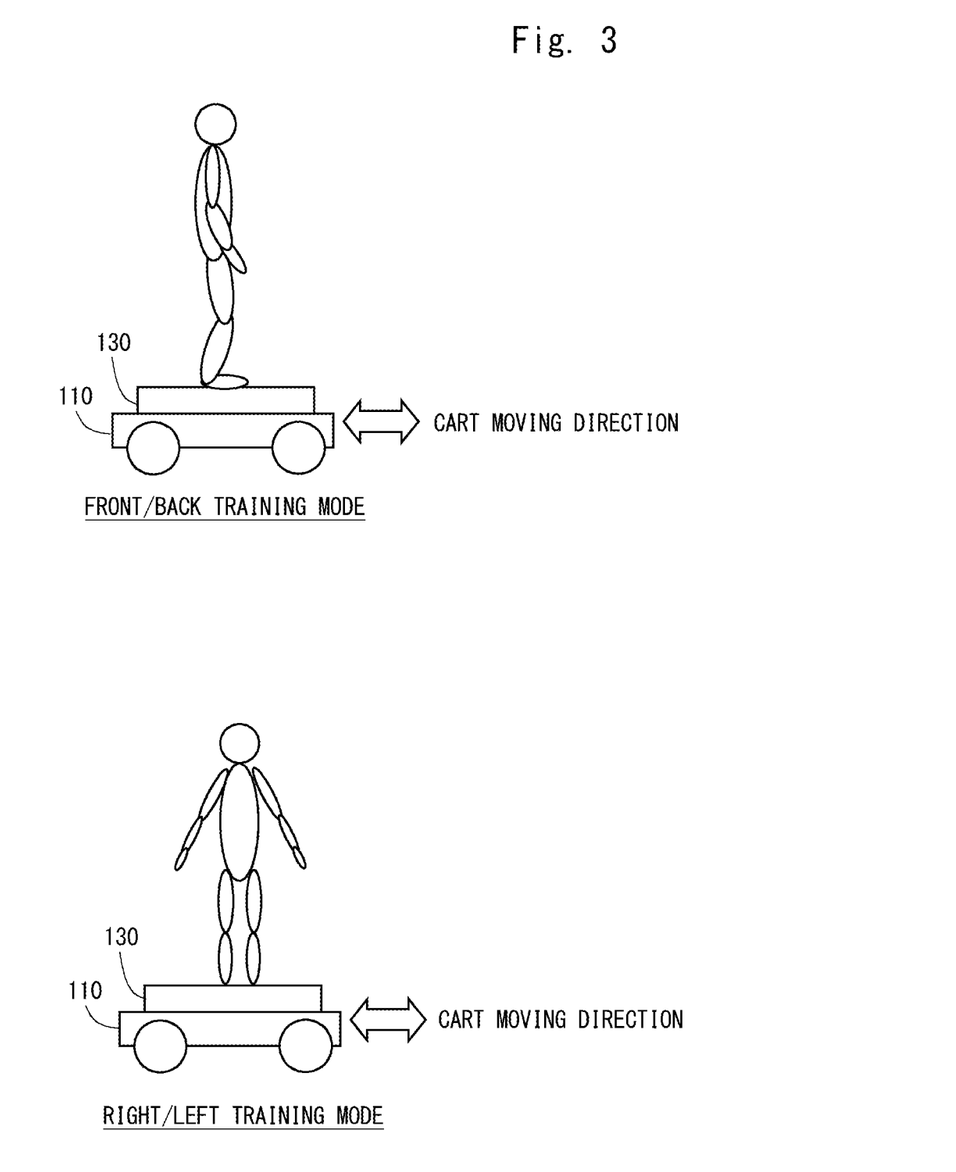
FIG. 3 is a diagram for describing training modes of the training apparatus according to the first embodiment.

Further, differences between the training modes in the training apparatus 100 according to the first embodiment will be explained. FIG. 3 shows a diagram for describing training modes of the balance training apparatus according to the first embodiment. As shown in FIG. 3, in the training apparatus 100 according to the first embodiment, there is a front/back training mode and a right/left training mode. Both the front back training mode and the right/left training mode are balance training performed in a state in which the trainee 900 stands on the riding plate 130 installed on the moving cart 110. In the front/back training mode, the balance training is performed in a state in which the front of the body of the trainee 900 is directed in the direction the same as that in which the moving cart 110 moves. On the other hand, in the right/left training mode, the balance training is performed in a state in which the front of the body of the trainee 900 is substantially orthogonal to the direction in which the moving cart 110 moves. In the training apparatus 100 according to the first embodiment, when the training mode is switched between the front/back training mode and the right/left training mode or when the training apparatus 100 is started to be used, the orientation of the body of the trainee 900 is determined from the moving direction of the center of gravity of the loads and the amount of movement, and moves the moving, cart 110 only when the orientation of the body of the trainee 900 matches the training mode.

Figure 4:
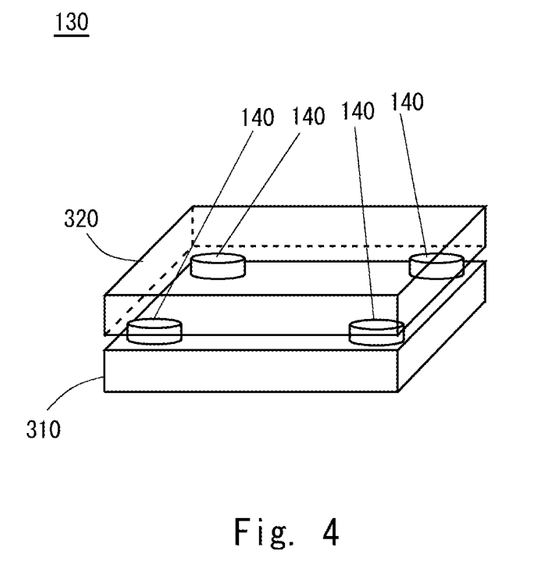
FIG. 4 is a schematic perspective view of a riding plate of the training apparatus according to the first embodiment.

Further, the details of the configuration of the riding plate 130 according to the first embodiment will be explained. FIG. 4 shows a schematic perspective view of the riding plate 130 of the training apparatus 100 according to the first embodiment. As shown in FIG. 4, the riding plate 130 includes a base plate 310 and a top plate 320. The base plate 310 is a surface that contacts the moving cart 110. The top plate 320 is a surface on which the trainee 900 rides. Then four load sensors 140 are provided in such a way that they are held between the base plate 310 and the top plate 320. The four load sensors 140 are arranged at four corners of the part where the base plate 310 is opposed to the top plate 320. Then the load calculation unit 201 calculates the center of gravity of the loads of the trainee 900 from the rate of the load information obtained from the four load sensors 140 and the location where the known load sensors 140 are arranged.

Figure 5:
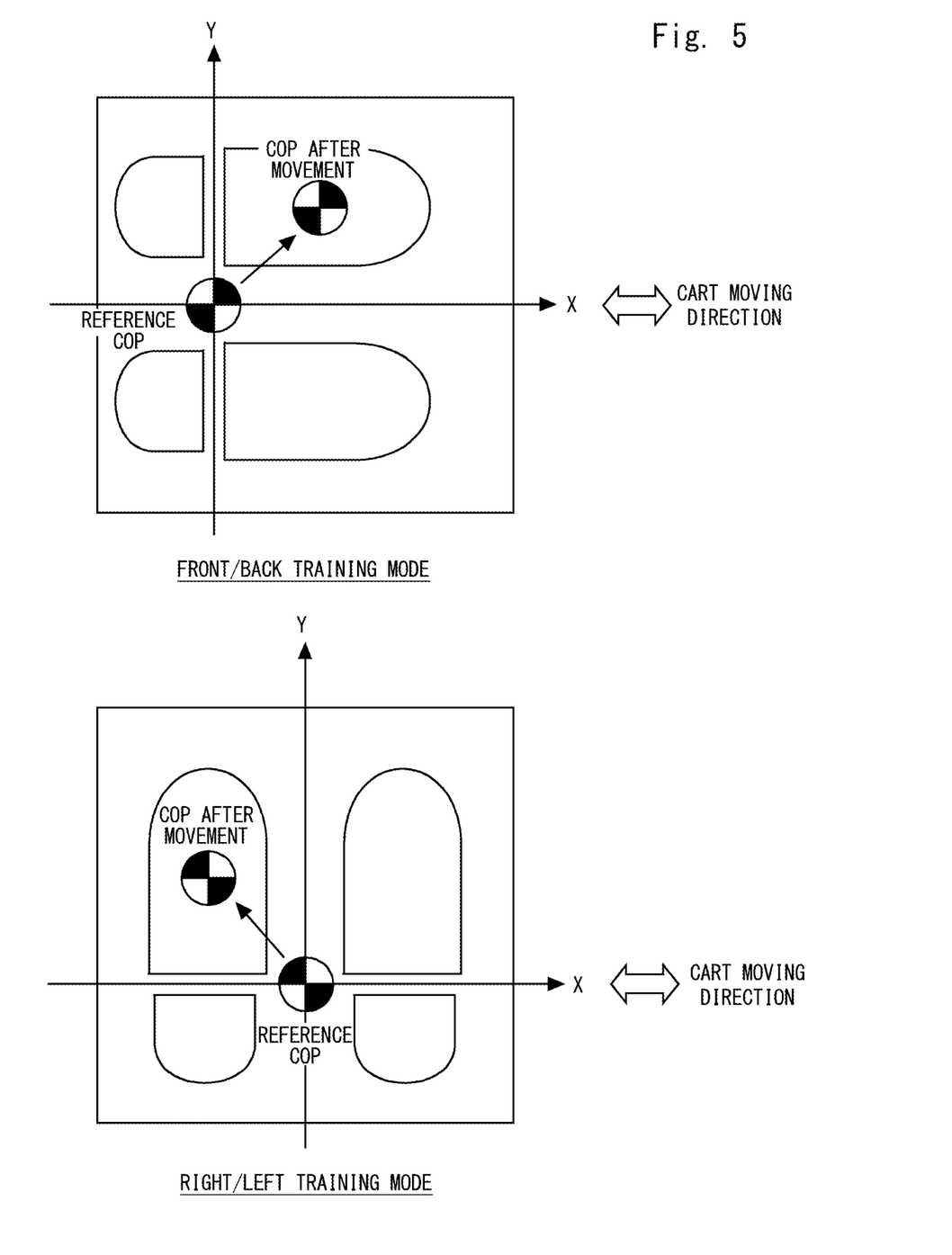
FIG. 5 is a diagram for describing a displacement direction of a center of gravity of the loads detected in the training apparatus according to the first embodiment.
Figure 6:
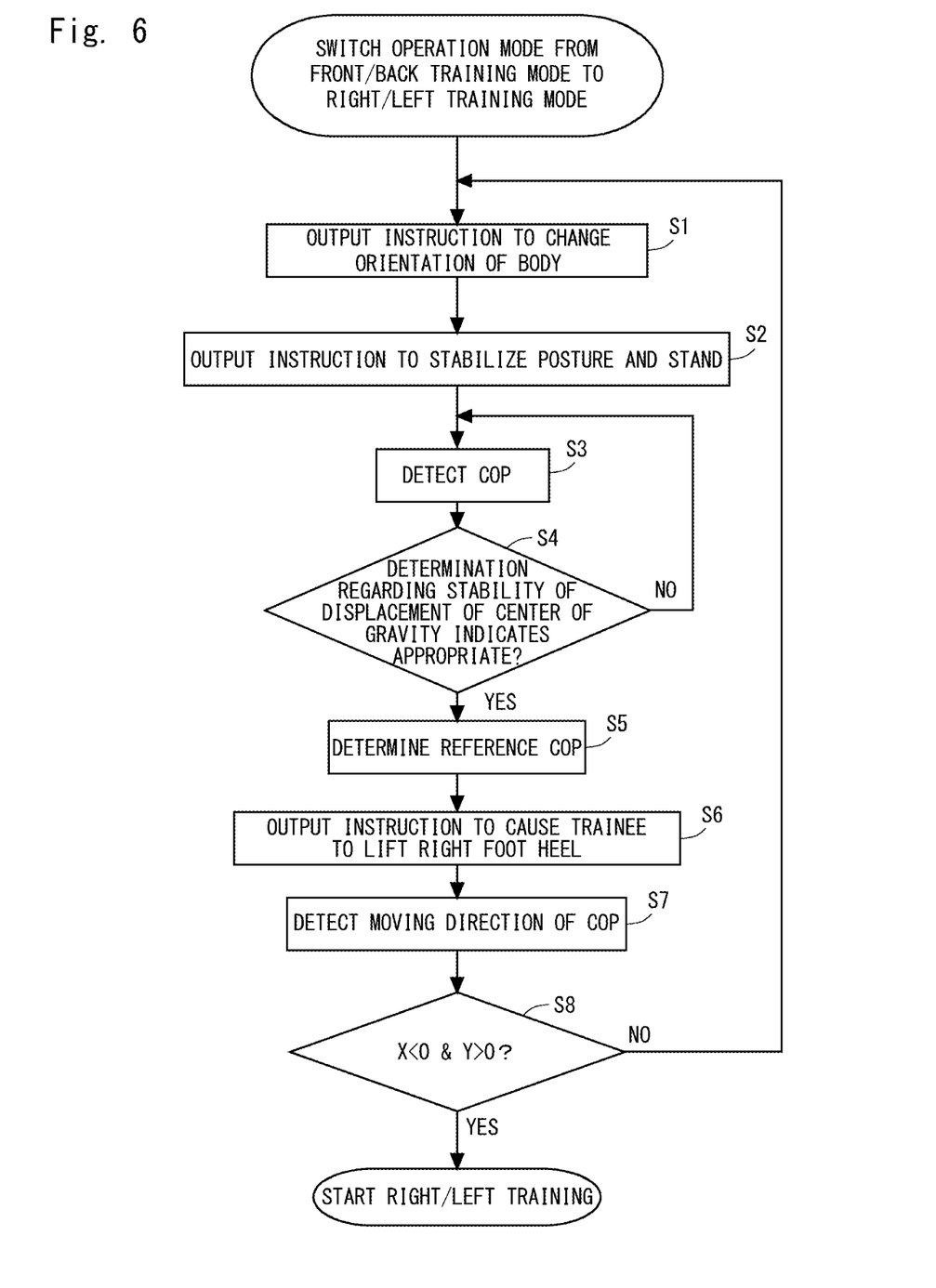
FIG. 6 is a flowchart for describing a procedure for switching a mode from a front/back training mode to a right/left training mode in the training, apparatus according to the first embodiment.

Next, a displacement direction of the center of gravity of the loads which serves as a reference for determining the orientation of the body of the trainee 900 in the training apparatus 100 according to the first embodiment will be explained, FIG. 5 shows a diagram for describing the displacement direction of the center of gravity of the loads detected in the training apparatus according to the first embodiment. As shown in FIG. 5, in the front/back training mode, the frontal direction of the body of the trainee 900 is directed to the direction that matches the direction in which the training apparatus 100 moves. Further, in the right/left training mode, the frontal direction of the body of the trainee 900 is directed to the direction that is substantially orthogonal to the direction in which the training apparatus 100 moves. At this time, the center of gravity of the loads when the trainee 900 stands upright becomes the reference center of gravity (reference COP in FIG. 5). In the training apparatus 100, the trainee 900 is instructed to move the center of gravity of the loads in a predetermined direction. The training apparatus 100 gives an instruction to the trainee 900, for example, to lift the right foot heel, After this instruction is given, the center of gravity of the loads of the trainee 900 moves in the left foot forward direction. Regarding the coordinates, in the front/back training, mode, the coordinates of the center of gravity of the loads are moved in the X-axis positive direction and the Y-axis positive direction. In the right/left training mode, the coordinates of the center of gravity of the loads are moved in the X-axis negative direction and the Y-axis positive direction, Next, the method of determining the orientation of the body of the trainee 900 before the start of the training in the training apparatus 100 according to the first embodiment will be explained. In this example, as one example of the method of determining the orientation of the body of the trainee 900, a method of determining the orientation of the body of the trainee 900 when the mode is switched from the front/back training mode to the right/left training mode will be explained. FIG. 6 shows a flowchart for describing a procedure for switching the mode from the front/back training mode to the right/left training mode in the training apparatus according to the first embodiment.

As shown in FIG. 6, first, the training apparatus 100 according to the first embodiment instructs, when the operation mode is switched from the front/back training mode to the right/left training mode, the trainee 900 to change the orientation of the body to the lateral direction (direction orthogonal to the direction in which the moving cart 110 moves) via the display controller 230 (Step S1). Further, the training apparatus 100 instructs the trainee 900 to stabilize his/her posture and stand on the riding plate 130 via the display controller 230 (Step S2).

The training apparatus 100 then performs detection of the center of gravity of the loads (COP in FIG. 5) by the load calculation unit 201 and determination regarding stability of the displacement of the center of gravity (Steps S3 and S4), When it is determined that the amount of the displacement of the center of gravity of the center of gravity of the loads is within a predetermined range, the load calculation unit 201 determines the coordinates of the reference center of gravity (reference COP in FIG. 5) (Step S5).

Next, the training apparatus 100 according to the first embodiment outputs an instruction to cause the trainee 900 to lift his/her right foot heel via the display controller 230 (Step S6), The training apparatus 100 then detects the center of gravity of the loads that has been moved since the trainee 900 has performed an operation of lifting his/her right foot heel in accordance with the instruction (Step S7), Then the load calculation unit 201 checks whether the moving direction of the center of gravity of the loads from the reference center of gravity is within an expected range (Step S8). In the example shown in FIG. 6, the trainee 900 takes a posture in accordance with the right/left training mode. In Step S8, since the X direction of the moving direction of the center of gravity of the loads becomes the negative direction and the Y direction thereof becomes the positive direction, the change of the posture is determined to be appropriate. In the example shown in FIG. 6, based on the results in Step S8 that the X direction of the moving direction of the center of gravity of the loads is the negative direction and the Y direction thereof is the positive direction, the training in the right/left training, mode is started. On the other hand, in the example shown in FIG. 6, when the X direction of the moving direction of the center of gravity of the loads is not the negative direction and the Y direction thereof is not the positive direction in Step S8, the training apparatus 100 performs the processing of instructing the trainee 900 to change his/her posture in Step S1 again.

From the above description, in the training apparatus 100 according to the first embodiment, as one of calibration processing before the balance training is started, it is determined whether the orientation of the body of the trainee 900 is directed to the direction in accordance with the training mode based on the moving direction of the center of gravity of the loads. Then the training apparatus 100 according to the first embodiment starts balance training when it is confirmed that the orientation of the body of the trainee 900 is directed to the direction in accordance with the training mode. Accordingly, the training apparatus 100 according to the first embodiment is able to prevent displacement between the posture in accordance with the training mode and the posture of the trainee 900 and to provide appropriate training for the trainee 900.

Further, in the training apparatus 100 according to the first embodiment, it is possible to check the posture of the trainee 900 using a detection value of the center of gravity of the loads that is necessary for balance training without depending on image processing and the like. That is, in the training apparatus 100 according to the first embodiment, it is not needed to add an additional apparatus for detecting the change in the posture.

Further, in the training apparatus 100 according to the first embodiment, it is possible to detect the moving direction of the center of gravity of the loads without causing the trainee to perform an operation whose load level is high for the trainee such as displacing the center of gravity of the trainee in the front-back direction or the right-left direction.

Second Embodiment

In a second, embodiment, another form of the method of determining the orientation of the body of the trainee 900 after the trainee is instructed to move his/her center of gravity of the loads will be explained. In the second embodiment, the trainee 900 is instructed to stabilize the center of gravity of the loads of the trainee 900 in a measurement start position using the load calculation unit 201 of the operation processing unit. 200 and the display controller 230. Specifically, the operation processing unit 200 instructs the display controller 230 to display the position of the center of gravity of the loads of the trainee 900, and after it is determined that the center of gravity of the loads of the trainee remains in a preset measurement start position for a predetermined period of time, the operation processing unit 200 instructs the display controller 230 to cause the trainee to move the center of gravity.

Figure 7:
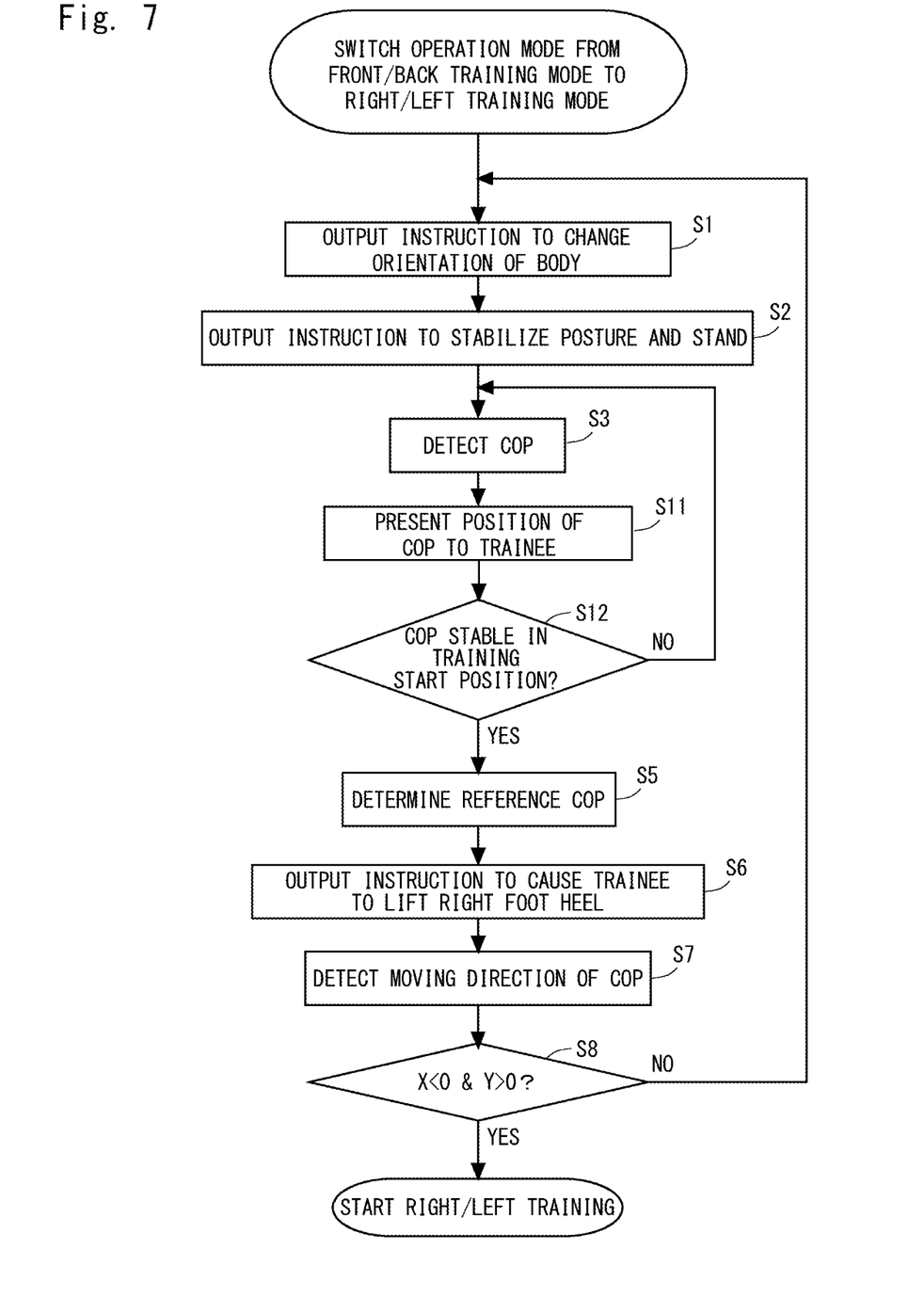
FIG. 7 is a flowchart for describing a procedure for switching, a mode from a front/back training mode to a right/left training mode in a training apparatus according to a second embodiment.

Now, a method of determining the orientation of the body of the trainee 900 before the training is started in the training apparatus 100 according to the second embodiment will be explained. In this example, as one example of the method of determining the orientation of the body of the trainee 900, a method of determining the orientation of the body of the trainee 900 when the mode is switched from the front/back training mode to the right/left training mode will be explained. FIG. 7 shows a flowchart for describing a procedure for switching the mode from the front/back training mode to the right/left training mode in the training apparatus according to the second embodiment.

As shown in FIG. 7, in the determination method according to the second embodiment, Step S4 shown in FIG. 6 is replaced by Steps S11 and S12, Step S11 is processing of displaying the position of the center of gravity of the loads detected by the load calculation unit 201 in Step 33 on the display controller 230. The training apparatus 100 according to the second embodiment determines the reference center of gravity of the loads after it is determined that the center of gravity of the loads is stable in the training start position for a predetermined period of time (Steps S12 and S5).

From the above description, the training apparatus 100 according to the second embodiment determines the reference center of gravity when the center of gravity of the loads of the trainee 900 is stably positioned in the preset training start position. Accordingly, in the training apparatus 100 according to the second embodiment, it is possible to determine the moving direction of the center of gravity of the loads more accurately than the training apparatus 100 according to the first embodiment.

A (The) program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A balance training apparatus comprising:
a moving cart capable of moving on a moving surface by driving a driving unit;
a detection unit configured to detect a load received from a foot of a trainee who is standing on the moving cart;
a calculation unit configured to calculate a center of gravity of loads of both feet of the trainee on a riding surface from the load detected by the detection unit;
a setting unit configured to set the center of gravity of the loads at which it is estimated that the trainee has maintained an upright state on the riding surface as a reference center of gravity; and
an instruction controller configured to output an instruction of an orientation of a body to the trainee and an instruction to move the center of gravity to the trainee,
wherein the calculation unit determines the orientation of the body of the trainee based on a change direction of the center of gravity of the loads from the reference center of gravity when the trainee has moved his/her center of gravity in accordance with the instruction from the instruction controller, and outputs an operation instruction to the driving unit when it is determined that a result of the determination is appropriate.

2. The balance training apparatus according to claim 1, wherein the setting unit sets the reference center of gravity based on the center of gravity of the loads calculated by the calculation unit in a calibration operation that the trainee performs prior to trial of the training.

3. The balance training apparatus according to claim 1, wherein the instruction controller outputs a center of gravity moving instruction to the trainee who is in an upright state to cause the trainee to move one foot, and
the calculation unit outputs the operation instruction to the driving unit when a displacement direction of the center of gravity of the loads of the trainee from the reference center of gravity after the instruction for moving the center of gravity is a direction along a preset displacement direction.

4. The balance training apparatus according to claim 1, wherein the calculation unit switches a front/back training mode in which a frontal direction of the body of the trainee matches a moving direction of the moving cart and a right/left training mode in which the frontal direction of the body of the trainee is substantially orthogonal to the moving direction of the moving cart based on an external instruction.

5. The balance training apparatus according to claim 1, wherein the calculation unit instructs the instruction controller to display a position of the center of gravity of the loads of the trainee, and after it is determined that the center of gravity of the loads of the trainee remains in a preset measurement start position for a predetermined period of time, the calculation unit instructs the instruction controller to cause the trainee to move the center of gravity.

6. A non-transitory computer readable medium storing a control program of a balance training apparatus in which a trainee who is standing on a moving cart that moves on a moving surface performs balance training, the control program causing a computer to execute the following steps:
a center of gravity calculation step for calculating the center of gravity of loads of both feet of the trainee on a riding surface from a load detected by a detection unit mounted on the moving cart;
a reference center of gravity setting step for setting the center of gravity of the loads at which it is estimated that the trainee has maintained an upright state on the riding surface as a reference center of gravity;
an instruction control step for outputting an instruction of an orientation of a body to the trainee and an instruction to move the center of gravity to the trainee; and
a control determination step for determining the orientation of the body of the trainee based on a change direction of the center of gravity of the loads from the reference center of gravity when the trainee has moved his/her center of gravity in the instruction output in the instruction control step and performing control to move the moving cart when it is determined that a result of the determination is appropriate.

* * * * *